United States Patent
Aubrun-Sonneville et al.

(10) Patent No.: US 10,617,623 B2
(45) Date of Patent: Apr. 14, 2020

(54) PEELING PROCESS WITH SURFACTANTS

(75) Inventors: Odile Aubrun-Sonneville, Antony (FR); Michelle Rathman Josserand, La Celle St Cloud (FR)

(73) Assignee: L'OREAL, Paris (FR)

( * ) Notice: Subject to any disclaimer, the term of this patent is extended or adjusted under 35 U.S.C. 154(b) by 1264 days.

(21) Appl. No.: 11/842,321

(22) Filed: Aug. 21, 2007

(65) Prior Publication Data

US 2008/0200545 A1    Aug. 21, 2008

Related U.S. Application Data

(60) Provisional application No. 60/840,958, filed on Aug. 30, 2006.

(30) Foreign Application Priority Data

Aug. 23, 2006   (FR) ...................................... 06 53430

(51) Int. Cl.
| | | |
|---|---|---|
| *A61Q 19/10* | (2006.01) | |
| *A61K 47/34* | (2017.01) | |
| *A61K 47/26* | (2006.01) | |
| *A61K 47/00* | (2006.01) | |
| *A61K 31/19* | (2006.01) | |
| *A61P 17/00* | (2006.01) | |
| *A61K 8/60* | (2006.01) | |
| *A61K 8/44* | (2006.01) | |
| *A61K 8/46* | (2006.01) | |

(52) U.S. Cl.
CPC ................ *A61K 8/604* (2013.01); *A61K 8/44* (2013.01); *A61K 8/442* (2013.01); *A61K 8/463* (2013.01); *A61Q 19/10* (2013.01); *A61K 2800/28* (2013.01)

(58) Field of Classification Search
None
See application file for complete search history.

(56) References Cited

U.S. PATENT DOCUMENTS

| | | | | |
|---|---|---|---|---|
| 5,720,949 | A * | 2/1998 | Davis ......................... | 424/78.03 |
| 2003/0044366 | A1* | 3/2003 | Dole et al. ...................... | 424/63 |
| 2003/0152610 | A1* | 8/2003 | Rolf ..................... | A61K 8/0208 |
| | | | | 424/449 |
| 2005/0288429 | A1* | 12/2005 | Rymer et al. ................. | 524/557 |

FOREIGN PATENT DOCUMENTS

| | | |
|---|---|---|
| EP | 1 529 522 | 5/2005 |
| EP | 1 621 183 | 2/2006 |
| EP | 1 674 069 | 6/2006 |
| JP | 63189476 | * 2/1987 |
| WO | WO 2004/093838 | 11/2004 |
| WO | WO 2005/063198 | 7/2005 |
| WO | WO 2006/077156 | 7/2006 |

OTHER PUBLICATIONS

Ash, Michael; Ash, Irene. Handbook of Industrial Surfactants (4th Edition) 2005. Synapse Information Resources, Inc.. <http://app.knovel.com/hotlink/toc/id:kp HISE000G/handbook-industrial-surfactants.> select pages. Accessed Oct. 9, 2013.*

Westwood-Squibb. Ammonium Lactate: Lac-Hydrin. < http://www.pharmacy.umaryland.edu/programs/mhaformulary/formulary%20reviews/pdfs/1999/lachydrin.pdf> accessed Oct. 7, 2013.*

Park, A. et al., "Carbopol Aqua CC Polymer: The Premier Cationic Compatible Rheology Modifier for Low pH Formulations," Cosmetic Science Technology, Jul. 2006, pp. 241-248.*

Lubrizol. Technical Data Sheet. "Flow and Suspension Properties of Carbopol Polymers". Jan. 2002.*

Women Fitness. Face Masks <http://www.womenfitness.net/beauty/skin/face_masks.htm> available Apr. 8, 2004, accessed Dec. 4, 2015.*

The Herbarie. Emulsifiers with HLB Values <http://www.theherbarie.com/files/resourcecenter/formulating/Emulsifiers_HLB_Values.pdf>; accessed Mar. 16, 2017.*

Schmid-Wendtner MH1, Korting HC. "The pH of the skin surface and its impact on the barrier function." Skin Pharmacol Physiol. 2006;19(6):296-302. Epub Jul. 19, 2006. PMID: 16864974 (Year: 2006).*

U.S. Appl. No. 11/842,342, filed Aug. 21, 2007, Aubrun-Sonneville, et al.

* cited by examiner

*Primary Examiner* — Nicole P Babson
(74) *Attorney, Agent, or Firm* — Oblon, McClelland, Maier & Neustadt, L.L.P.

(57) ABSTRACT

Process for the treatment of, e.g., visible and/or tactile irregularities of human skin, by applying topically, to the skin, a composition containing, in a physiologically acceptable medium, at least 5% by weight of one or more surfactants comprising at least one alkyl chain having from 6 to 16 carbon atoms.

14 Claims, No Drawings

PEELING PROCESS WITH SURFACTANTS

REFERENCE TO PRIOR APPLICATIONS

This application claims priority to U.S. provisional application 60/840,958 filed Aug. 30, 2006, and to French patent application 0653430 filed Aug. 23, 2006, both incorporated herein by reference.

FIELD OF THE INVENTION

The present invention relates to a peeling process which uses a composition containing at least 5% of surfactants comprising at least one alkyl chain having from 6 to 16 carbon atoms.

Additional advantages and other features of the present invention will be set forth in part in the description that follows and in part will become apparent to those having ordinary skill in the art upon examination of the following or may be learned from the practice of the present invention. The advantages of the present invention may be realized and obtained as particularly pointed out in the appended claims. As will be realized, the present invention is capable of other and different embodiments, and its several details are capable of modifications in various obvious respects, all without departing from the present invention. The description is to be regarded as illustrative in nature, and not as restrictive.

BACKGROUND OF THE INVENTION

Peels are a well-known means for improving the surface appearance of the skin, in particular for treating visible and/or tactile irregularities of human skin, and, for example, reducing pigmentation defects such as actinic lentigo or acne or chickenpox marks, or for smoothing out skin texture irregularities, in particular wrinkles and fine lines.

These peels have the effect of removing a part of the skin to be treated (epidermis and, optionally, superficial layer of the dermis) by means of chemical methods such as the application of compositions containing high concentrations of agents for stimulating desquamation of the skin, such as hydroxy acids, for instance glycolic acid or salicylic acid, or else other active agents such as, for example, retinoic acid, resorcin, trichloroacetic acid or phenol. Thus, document U.S. Pat. No. 6,787,148 describes compositions containing anhydrous products containing a phenol and a polyethylene glycol derivative.

Although the compositions used up until now for carrying out chemical peels have been able to give satisfactory results, it nevertheless remains that they are not without side effects. Specifically, the products used for peels generally contain acidic keratolytic agents at high concentration, giving compositions of pH<2, and as a result they bring about considerable discomfort upon application and after application (redness, stinging, burning sensation). Thus, salicylic acid peels can give rise to salicylism in the event of overdose or of sustained application.

SUMMARY OF THE INVENTION

There remains therefore the need to have peeling compositions which are effective while at the same time being better tolerated.

In this regard, the inventors have discovered that compositions comprising at least 5% by weight of one or more surfactants comprising at least one alkyl chain having from 6 to 16 carbon atoms answer this problem.

Nothing in the prior art would suggest that surfactants having a $C_6$-$C_{16}$ alkyl chain could be used to carry out chemical peels for cosmetic purposes.

DETAILED DESCRIPTION OF THE PREFERRED EMBODIMENTS

One subject of the invention is a process for the treatment of visible and/or tactile irregularities of human skin, comprising applying topically, to the skin, a composition comprising, in a physiologically acceptable medium, at least 5% by weight of one or more surfactants comprising at least one alkyl chain having from 6 to 16 carbon atoms, relative to the total weight of the composition. It is of course preferred that the user leave the composition in contact with the skin for a period of time sufficient for the composition to act, and also preferable that the user remove the composition, for example by rinsing.

This process can be envisaged in one embodiment as comprising:
  (a) applying topically, to the skin, a composition comprising, in a physiologically acceptable medium, at least 5% by weight of one or more surfactants comprising at least one alkyl chain having from 6 to 16 carbon atoms, relative to the total weight of the composition,
  (b) leaving the composition in contact with the skin for a period of time sufficient for the composition to act, and
  (c) optionally, removing the composition by rinsing.

When the composition is left in contact with the skin for an application time which should be sufficient for the composition to act on the visible and/or tactile irregularities of the skin, this time will vary according to the concentration of surfactants in the composition, and to the desired effect. By way of example, the composition may remain in contact with the skin or the integuments for a period of, e.g., a minute or two, 5 minutes, generally between 5 minutes and 12 hours, preferably between 5 minutes and 6 hours, preferentially between 5 minutes and 30 minutes. The composition may or may not be removed at the end of this period of contact. The application may be daily or twice-daily, or even more frequently or, e.g., weekly, and repeated for periods of, e.g., 2 weeks to 6 months, it being possible for this period to be prolonged or renewed without difficulty.

Unlike a cleansing composition which is immediately rinsed off after application to the skin, the present composition should remain on the skin for a period of time. This time allows for the surfactants to interact with the irregularities of the skin and to fade them out by virtue of a peeling effect (desquamation). Generally speaking, the longer the time of interaction the more effect observed.

A subject of the invention is also a peelant composition comprising at least 5% by weight of one or more surfactants comprising an alkyl chain having from 6 to 16 carbon atoms in a physiologically acceptable medium, useful as an agent for stimulating skin desquamation.

Since the composition is for topical application, it comprises a physiologically acceptable medium. The term "physiologically acceptable medium" is intended to mean a medium compatible with keratin materials such as the skin, the lips, the nails, the scalp and/or the hair. The composition is in particular a cosmetic or dermatological composition.

The medium is an aqueous medium, i.e. it contains water, the amount of which is preferably at least 20% by weight relative to the total weight of the composition. The amount of water can, for example, range from 20% to 95% by weight or more, preferably from 30% to 90% by weight, and better still from 35% to 80% by weight, relative to the total weight of the composition.

The composition is preferably free of hydroxy acid. The term "composition free of hydroxy acid" is intended to mean a composition which contains neither α-hydroxy acid such as glycolic acid and lactic acid, nor β-hydroxy acid such as salicylic acid, or which contains said acids in a minimal amount, for example when they are present as pH modifiers or preservatives. The term "minimal amount" is intended to mean an amount of less than 3%, preferably less than 2%, better still less than 1%, and even better still less than 0.5%, including less than 0.4, 0.3, 0.2, 0.1 etc. %, of the total weight of the composition.

The composition preferably has a pH compatible with the skin. This pH can range from 2 to 9, preferably from 2.5 to 8, and better still from 3.5 to 7.

Surfactants

The composition according to the invention comprises one or more surfactants comprising at least one alkyl chain having from 6 to 16 carbon atoms, preferably from 6 to 14 carbon atoms.

The surfactant or the mixture of surfactants preferably has an HLB (hydrophilic lipophilic balance) of greater than 8, preferably an HLB of at least 9. Surfactants having an HLB of less than or equal to 8 can also be used, especially when one or more other surfactants are added thereto, such that the HLB of the mixture is greater than 8.

The surfactants used according to the present invention can be chosen from nonionic, anionic, cationic, amphoteric or zwitterionic surfactants, and mixtures thereof. They can be obtained from alcohols, from acids, from amines, from amides, from alkyl glycerols and from any radical comprising at least one alkyl chain ranging from $C_6$ to $C_{16}$, preferably from $C_6$ to $C_{14}$ including all of C6, C7, C8, C9, C10, C11, C12, C13, C14, C15 and C16.

The polar portion of these surfactants may be nonionic, anionic, cationic and amphoteric or zwitterionic.

The nonionic surfactants can be chosen from surfactants comprising a group chosen, for example, from polyalkylene glycol groups, such as, in particular, polyethylene glycol or polypropylene glycol; polyglycerol groups; sugar groups (glucose, maltose, sorbitol, ethoxylated sorbitan); and mixtures thereof.

The anionic surfactants can be chosen from surfactants comprising a group chosen, for example, from sulphate groups, sulphonate groups, phosphate groups, carboxylate groups, amino acid groups such as glycinate, glutamate and derivatives of these amino acids, in particular salts thereof, and mixtures thereof.

The cationic surfactants can be chosen from surfactants comprising, for example, a quaternary ammonium group.

The amphoteric or zwitterionic surfactants can be chosen from surfactants comprising a group chosen, for example, from amphoacetate groups, amphodiacetate groups, betaine groups and sultaine groups.

The composition can contain a mixture of these various types of surfactants.

As nonionic surfactants, mention may, for example, be made of:
  alkyl polyglycosides, and in particular alkyl polyglucosides (APGs) having an alkyl group containing from 6 to 16 carbon atoms ($C_6$-$C_{16}$ alkyl polyglucosides), and preferably 8 to 16 carbon atoms, for instance the decylglucoside (alkyl-$C_9$/$C_{11}$-polyglucoside (1.4)) such as the product sold under the name Mydol 10 by the company Kao Chemicals, the product sold under the name Plantaren 2000 UP or Plantacare 2000 UP by the company Cognis, and the product sold under the name Oramix NS 10 by the company Seppic; caprylyl/capryl glucoside, for instance the product sold under the name Oramix CG 110 by the company Seppic; lauryl glucoside, for instance the products sold under the names Plantaren 1200 N and Plantacare 1200 by the company Cognis; and cocoglucoside, for instance the product sold under the name Plantacare 818/UP by the company Cognis;

esters of polyethylene glycol and of acids comprising at least one alkyl chain ranging from $C_6$ to $C_{16}$, preferably from $C_6$ to $C_{14}$, such as polyethylene glycol (8 EO) myristate, for instance the product sold by the company Gattefosse under the name Mirlene;

ethers of polyethylene glycol and of alcohols comprising at least one alkyl chain ranging from $C_6$ to $C_{16}$, preferably from $C_6$ to $C_{14}$, such as the laureth-4 sold by the company Uniqema under the name Brij 30, or the laureth-23 sold by the company Uniqema under the name Brij 35;

derivatives of polyethylene glycol and of mono-, di- and triglycerides of an acid comprising at least one alkyl chain ranging from $C_6$ to $C_{16}$, preferably from $C_6$ to $C_{14}$, and having at least two ethylene oxide groups, and preferably from 6 to 8 ethylene oxide groups, such as mono-, di- and triglycerides of caprylic acid and of capric acid, for instance that comprising 6 ethylene oxide groups (INCI name: PEG-6 caprylic/capric glycerides), sold under the name Softigen 767 by the company Sasol, that comprising 8 ethylene oxide groups (INCI name: PEG-8 caprylic/capric glycerides), sold under the name L.A.S. by the company Gattefosse, and that comprising 7 ethylene oxide groups, sold under the name Cetiol HE 810 by the company Cognis (INCI name: PEG-7 caprylic/capric glycerides); the oxyethylenated (20 EO) glyceryl monolaurate sold under the name Tagat L 2 by the company Degussa-Goldschmidt;

oxyethylenated derivatives of sorbitan esters of an acid comprising at least one alkyl chain ranging from $C_6$ to $C_{16}$, preferably from $C_6$ to $C_{14}$, such as the PEG-10 sorbitan laurate sold under the name Liposorb L10 by the company Lipo Chemicals;

sugar esters comprising at least one $C_6$ to $C_{16}$ alkyl chain, such as the mixture of sucrose laurate and sucrose dilaurate, sold by the company Mitsubishi Chemical under the name Surfhope SE Cosme C-1216;

esters of polyglycerol and of an acid comprising at least one $C_6$ to $C_{16}$ alkyl chain, such as the polyglycerol monolaurate (10 mol of glyceryl) (INCI name: polyglyceryl-10 laurate) sold by the company Sakamoto Yakuhin under the name S Face L-1001;

polyglyceryl ethers, such as the polyglycerol-3 hydroxylauryl ether produced by Chimex under the name Chimexane NF;

and mixtures thereof.

As anionic surfactants, mention may, for example, be made of:
  alkyl sulphates, alkyl ether sulphates and their salts, in particular their sodium salts, for instance sodium lauryl ether sulphate such as the product sold under the name Texapon AOS 225 UP by the company Cognis;

monoalkyl and dialkyl esters of phosphoric acid, and their salts, for instance sodium mono- and dilauryl phosphate, potassium mono- and dilauryl phosphate, triethanolamine mono- and dilauryl phosphate, sodium mono- and dimyristyl phosphate, potassium mono- and dimyristyl phosphate, diethanolamine mono- and dimyristyl phosphate, triethanolamine mono- and dimyristyl phosphate;

amino acid derivatives, in particular the alkali metal salts of amino acids, such as:

acyl sarcosinates, such as the sodium lauroyl sarcosinate sold under the name Sarkosyl NL 97 by the company Ciba or sold under the name Oramix L 30 by the company Seppic, the sodium myristoyl sarcosinate sold under the name Nikkol Sarcosinate MN by the company Nikkol, the sodium palmitoyl sarcosinate sold under the name Nikkol Sarcosinate PN by the company Nikkol;

acyl alaninates, such as the sodium N-lauroyl-N-methyl amidopropionate sold under the name Sodium Nikkol Alaninate LN 30 by the company Nikkol, or sold under the name Alanone ALE by the company Kawaken, the N-lauroyl-N-methyl alanine triethanolamine sold under the name Alanone Alta by the company Kawaken;

acyl glutamates, such as the triethanolamine monococoyl glutamate sold under the name Acylglutamate CT-12 by the company Ajinomoto, the triethanolamine lauroyl glutamate sold under the name Acylglutamate LT-12 by the company Ajinomoto;

acyl glycinates, such as the sodium N-cocoyl glycinate sold under the names Amilite GCS-12 and Amilite GCK 12 by the company Ajinomoto;

alkyl ether carboxylates, in particular those of formula:

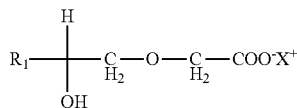

in which:

$R_1$ denotes more particularly a linear or branched, saturated or unsaturated alkyl radical containing from 8 to 16 carbon atoms, X denotes hydrogen or a mineral or organic cation such as those derived from an alkali metal (for example, $Na^+$ or $K^+$), $NH_4^+$, ammoniums derived from basic amino acids such as lysine, arginine, sarcosine, ornithine or citrulline, or alternatively amino alcohols such as monoethanolamine, diethanolamine, triethanolamine, glucamine, N-methylglucamine or 3-amino-1,2-propanediol. Preferred 2-hydroxy alkyl ether carboxylic acids are compounds of formula (I) in which R1 denotes more particularly a mixture of $C_8$-$C_{16}$ radicals, in particular derived from coconut. Among the surfactants of formula (I), mention may in particular be made of the product sold under the name Beaulight Shaa by the company Sanyo;

and mixtures thereof.

The cationic surfactants that can be used according to the present invention may in particular be primary, secondary or tertiary amine salts comprising a $C_6$ to $C_{16}$ alkyl chain, which are optionally polyoxyalkylenated; quaternary ammonium salts; imidazoline derivatives or amine oxides that are cationic in nature.

In the quaternary ammonium salts, the anion is preferably a halide (chloride, bromide or iodide) or an alkyl sulphate, more particularly a methyl sulphate. It is, however, possible to use quaternary ammonium salts in which the anion is a methanesulphonate, a phosphate, a nitrate, a tosylate, an anion derived from an organic acid, such as acetate or lactate, or any other anion compatible with the ammonium comprising an ester function. The anion is even more particularly chloride or methyl sulphate.

Among the quaternary ammonium salts, mention may in particular be made of:

tetraalkylammonium chlorides such as, for example, dialkyldimethylammonium chloride or alkyltrimethylammonium chloride, in which the alkyl radical contains approximately from 6 to 16 carbon atoms, for instance the dodecyltrimethylammonium chloride sold under the name Arquad 12-50 by the company Akzo Nobel, or the cetyltrimethylammonium chloride sold under the name Dehyquart A OR by the company Cognis;

quaternary ammonium salts containing at least one ester function, for example the dicocoylethylhydroxyethylmethylammonium methosulphate sold under the name Dehyquart L 80 by the company Cognis;

quaternary ammonium salts containing a sugar unit, for example a glucose, fructose or sucrose unit, for instance the butyldimoniumhydroxypropyl laurylglucoside chloride (INCI name: butyldimoniumhydroxypropyl laurylglucoside chloride) sold under the name Colonial SugaQuat TM-1212 by the company Colonial Chemical Inc, the lauryl methyl gluceth-10 hydroxypropyldimonium chloride (INCI name: lauryl methyl gluceth-10 hydroxypropyldimonium chloride) sold under the name Glucquat 125 by the company Noveon.

The amphoteric and zwitterionic surfactants can be chosen, for example, from betaine derivatives, and in particular alkylated derivatives of betaine, alkylamidopropylbetaines, alkylamphoacetates, hydroxysultaines, and mixtures thereof.

As betaine derivatives, mention may in particular be made of alkylbetaines comprising a $C_6$-$C_{16}$, and more particularly $C_6$-$C_{14}$, alkyl group, and oxyethylenated derivatives thereof, for example cocobetaine, for instance the product sold under the name Dehyton AB-30 by the company Cognis, laurylbetaine, for instance the product sold under the name Genagen KB by the company Clariant, or oxyethylenated (10 EO) laurylbetaine, for instance the product sold under the name Laurylether (10 EO) Betaine by the company Shin Nihon Rica.

As alkylamidopropylbetaines, mention may, for example, be made of ($C_6$-$C_{16}$)alkylamidopropylbetaines such as the cocamidopropyl betaine sold, for example, under the name Velvetex BK 35 by the company Cognis or else the undecylenamidopropyl betaine sold, for example, under the name Amphoram U by the company Ceca.

As alkylamphoacetates, mention may, for example, be made of ($C_6$-$C_{16}$)alkylamphoacetates, such as N-disodium N-cocoyl-N-carboxymethoxyethyl-N-carboxymethylethylene-diamine (INCI name: disodium cocamphodiacetate), for instance the product sold under the name Miranol C2M Concentrate NP by the company Rhodia Chimie, and N-sodium N-cocoyl-N-hydroxyethyl-N-carboxymethyl-ethylenediamine (INCI name: sodium cocamphoacetate).

The composition used in the process according to the present invention contains an amount of surfactant(s) which should be adjusted according to the surfactant(s) used, according to the strength of the peel which is to be carried out and according to the type of skin to which the composition is applied. This amount is at least 5% by weight, and preferably at least 10% by weight, relative to the total weight of the composition. It can range, for example, from 5% to 70% by weight, preferably from 10% to 60% by weight, better still from 10% to 50% by weight, even better still from 13% to 50% by weight, and even from 15% to 50% by weight, relative to the total weight of the composition.

The composition according to the invention can be applied by any way which allows an even distribution over the skin, and in particular using the fingers, cotton wool, a cotton wool bud, a brush, a gauze, a spatula or a pad, or else by spraying, and it may or may not be removed. It can be removed, for example, by rinsing with water or simply wiping.

The compositions according to the invention may be in any form, including any of the pharmaceutical forms used in the cosmetics and dermatological fields, in particular in the form of aqueous gels, of lotions or of emulsions. These compositions are prepared according to the usual methods. According to a preferred embodiment of the invention, the composition is in the form of an aqueous, aqueous-alcoholic or aqueous-glycolic gel, or of an aqueous, aqueous-alcoholic or aqueous-glycolic solution.

When the composition according to the invention comprises an oily phase, in particular when it is in the form of an emulsion, the oily phase preferably contains at least one oil, in particular a physiologically acceptable oil. It can also contain other fatty substances.

As oils that can be used in the composition of the invention, mention may, for example, be made of:
  hydrocarbon-based oils of animal origin, such as perhydrosqualene;
  hydrocarbon-based oils of plant origin, such as liquid triglycerides of fatty acids containing from 4 to 10 carbon atoms, for instance heptanoic acid or octanoic acid triglycerides, or else, for example, sunflower oil, maize oil, soybean oil, marrow oil, grapeseed oil, sesame oil, hazelnut oil, apricot oil, macadamia oil, arara oil, castor oil, avocado oil, caprylic/capric acid triglycerides such as those sold by the company Stearineries Dubois or those sold under the names Miglyol 810, 812 and 818 by the company Dynamit Nobel, jojoba oil, shea butter oil;
  synthetic esters and ethers, in particular of fatty acids, such as oils of formulae $R^1COOR^2$ and $R^1OR^2$ in which $R^1$ represents the residue of a fatty acid containing from 8 to 29 carbon atoms, and $R^2$ represents a branched or unbranched hydrocarbon-based chain containing from 3 to 30 carbon atoms, for instance purcellin oil, isononyl isononanoate, isopropyl myristate, 2-ethylhexyl palmitate, 2-octyldodecyl stearate, 2-octyldodecyl erucate, isostearyl isostearate, isocetyl stearate; hydroxylated esters such as isostearyl lactate, octyl hydroxystearate, octyldodecyl hydroxystearate, diisostearyl malate, triisocetyl citrate, fatty alcohol heptanoates, octanoates and decanoates; polyol esters, such as propylene glycol dioctanoate, neopentyl glycol diheptanoate and diethylene glycol diisononanoate; and pentaerythrityl esters such as pentaerythrityl tetraisostearate;
  linear or branched hydrocarbons of mineral or synthetic origin, such as volatile or non-volatile paraffin oils, and derivatives thereof, petroleum jelly, polydecenes, hydrogenated polyisobutene such as parleam oil;
  fatty alcohols containing from 8 to 26 carbon atoms, such as cetyl alcohol, stearyl alcohol and the mixture thereof (cetylstearyl alcohol), octyldodecanol, 2-butyloctanol, 2-hexyldecanol, 2-undecylpentadecanol, oleyl alcohol or linoleyl alcohol;
  partially hydrocarbon-based and/or silicone-based fluoro oils such as those described in document JP-A-2-295912;
  silicone oils such as volatile or non-volatile polymethylsiloxanes (PDMSs) containing a linear or cyclic silicone chain, which are liquid or pasty at ambient temperature, in particular cyclopolydimethylsiloxanes (cyclomethicones) such as cyclohexasiloxane; polydimethylsiloxanes comprising alkyl, alkoxy or phenyl groups which are pendent or at the end of the silicone chain, which groups contain from 2 to 24 carbon atoms; phenyl silicones such as phenyl trimethicones, phenyl dimethicones, phenyltrimethylsiloxydiphenylsiloxanes, diphenyl dimethicones, diphenylmethyldiphenyltrisiloxanes, 2-phenylethyltrimethylsiloxysilicates, and polymethylphenylsiloxanes;
  lipophilic derivatives of amino acids, in particular those described in document FR-A-2 796 550, which is incorporated herein by way of reference, and in particular isopropyl N-lauroylsarcosinate;
  mixtures thereof.

The term "hydrocarbon-based oil" in the list of oils mentioned above is intended to mean any oil containing predominantly carbon and hydrogen atoms and, optionally, ester, ether, fluoro, carboxylic acid and/or alcohol groups.

The other fatty substances that may be present in the oily phase are, for example, fatty acids containing from 8 to 30 carbon atoms, for instance stearic acid, lauric acid, palmitic acid and oleic acid; waxes such as lanolin, beeswax, carnauba wax or candelilla wax, paraffin wax, lignite wax or microcrystalline waxes, ceresin or ozokerite, synthetic waxes such as polyethylene waxes, Fischer-Tropsch waxes; silicone resins such as trifluoromethyl($C_1$-$C_4$)alkyl dimethicone and trifluoropropyl dimethicone; and silicone elastomers such as the products sold under the name "KSG" by the company Shin-Etsu, under the names "Trefil", "BY29" or "EPSX" by the company Dow Corning or under the name "Gransil" by the company Grant Industries.

These fatty substances can be chosen in a varied manner by those skilled in the art in order to prepare a composition having the desired properties of, for example, consistency or texture.

When the composition is in the form of an emulsion, it is preferably an oil-in-water (O/W) emulsion. The emulsions generally contain at least one emulsifier chosen in particular from amphoteric, anionic, cationic or nonionic emulsifiers, used alone or as a mixture. They are preferably nonionic emulsifiers. These emulsifiers are chosen from those conventionally used in the cosmetics field.

It is also possible to prepare emulsions without emulsifying surfactants, or containing less than 0.5% thereof, with respect to the total weight of the composition, using appropriate compounds, for example polymers having emulsifying properties, such as the polymers sold under the names Carbopol 1342 and Pemulen by the company Noveon; or optionally crosslinked and/or neutralized polymers and copolymers of 2-acrylamido-2-methylpropanesulphonic acid, such as the poly-(2-acrylamido-2-methylpropanesulphonic acid) sold by the company Clariant under the name "Hostacerin AMPS" (INCI name: ammonium polyacryldimethyltauramide) or such as the emulsion polymer sold under the name Sepigel 305 by the company Seppic (INCI name: polyacrylamide/C13-C14 isoparaffin/laureth-7); particles of ionic or nonionic polymers, more particularly particles of anionic polymer, such as in particular isophthalic acid or sulphoisophthalic acid polymers, and in particular phthalate/sulphoisophthalate/glycol copolymers (for example, diethylene glycol/phthalate/isophthalate/1,4-cyclohexanedimethanol copolymers (INCI name: diglycol/CHDM/isophthalates/SIP copolymer) sold under the names Eastman AQ polymer (AQ35S, AQ38S, AQ55S, AQ48 Ultra) by the company Eastman Chemical.

It is also possible to prepare emulsions without emulsifiers, stabilized with silicone particles or particles of metal oxide such as $TiO_2$ or the like, which may or may not be coated.

In a known manner, the composition of the invention may also contain adjuvants that are normal in the cosmetics or dermatological field, such as hydrophilic or lipophilic gelling agents, hydrophilic or lipophilic active agents, preserving agents (for example, phenoxyethanol and parabens), antioxidants, solvents, fragrances, fillers, bactericides, odour absorbers, dyestuffs, pH modifiers (acid or base or buffer). The amounts of these various adjuvants are those conventionally used in the field under consideration, and for example from 0.01 to 20% of the total weight of the composition. Depending on their nature, these adjuvants can be introduced into the oily phase or into the aqueous phase, or solubilized in the surfactants.

Of course, those skilled in the art will take care to select the optional additive(s) to be added to the composition according to the invention, and the amounts thereof, in such a way that the advantageous properties intrinsically associated with the composition in accordance with the invention are not, or not substantially, impaired by the envisaged addition.

According to a specific embodiment of the invention, the composition contains at least one hydrophilic polymer, i.e. water-soluble or water-dispersible polymer. As hydrophilic polymers, mention may in particular be made of:
  cellulose-based derivatives (carboxymethylcellulose, hydroxyethylcellulose, hydroxypropylmethylcellulose);
  natural gums such as xanthan gum, guar gum, carob gum or carageenans;
  polycarboxyvinyl polymers of the carbomer type, such as those sold by the company Goodrich under the names Carbopol 940, 951 and 980, or by the company 3V-Sigma under the name Synthalen K or Synthalen L;
  acrylic copolymers such as the acrylate/alkyl acrylate copolymers sold under the name Pemulen by the company Goodrich;
  polyacrylamides and acrylamide copolymers, indicated above, such as the product sold under the name Sepigel 305 by the company Seppic, the product sold under the name Hostacerin Amps by the company Clariant or the copolymers sold under the name Aristoflex by the company Clariant.

The amount of hydrophilic polymer(s) can range, for example, from 0.01% to 5% by weight, preferably from 0.05% to 5% by weight, and better still from 0.1% to 3% by weight, relative to the total weight of the composition.

Moreover, the composition can also contain at least one water-soluble hydroxylated compound chosen from $C_2$-$C_6$, and preferably $C_2$-$C_4$, monohydric alcohols such as ethanol and isopropanol, and polyols containing from 1 to 3 carbon atoms, such as glycerol, propylene glycol, butylene glycol, dipropylene glycol or isopropylene glycol; and mixtures thereof. The amount of hydroxylated compound(s) can range, for example, from 0.1% to 75% by weight, better still from 1% to 70% by weight, and even better still from 1% to 50% by weight, relative to the total weight of the composition.

When the composition is aqueous-alcoholic, it contains water and at least one monohydric alcohol, and when the composition is aqueous-glycolic, it contains water and at least one polyol. It can of course contain both alcohols and polyols.

The composition can also contain any appropriate active agent(s), such as, for example, urea and its hydroxylated derivatives such as the N-(2-hydroxyethyl)urea sold under the name Hydrovance by the company National Starch; hyaluronic acid; hydrating polymers such as acrylic polymers comprising a phosphorylcholine group, such as:
  the poly-2-(methacryloyloxyethyl)phosphorylcholine at 40% in a water/butanediol mixture (5% of butanediol) sold under the name Lipidure HM by the company Nippon Oils and Fats (INCI name: polyphosphorylcholine glycol acrylate (and) butylene glycol);
  the 2-(methacryloyloxyethyl)phosphorylcholine/butyl methacrylate (90/10) copolymer at 5% in solution in water, sold under the name Lipidure PMB by the company Nippon Oils and Fats (INCI name: Polyquaternium-51);
  the 2-(methacryloyloxyethyl)phosphorylcholine/2-hydroxy-3-methacryloyloxypropyltrimethylammonium chloride copolymer at 5% in solution in water, sold under the name Lipidure-C by the company Nippon Oils and Fats;
  the 2-(methacryloyloxyethyl)phosphorylcholine/butyl methacrylate/sodium methacrylate terpolymer at 5% in solution in water, sold under the name Lipidure-A by the company Nippon Oils and Fats;
  the 2-(methacryloyloxyethyl)phosphorylcholine/stearyl methacrylate copolymers sold under the names Lipidure-S, Lipidure-NR and Lipidure-NA by the company Nippon Oils and Fats (INCI name: Polyquaternium-61).

The composition may also contain other active agents such as vitamins, for instance vitamins A, C, E, B3, B5 and K, and derivatives thereof, in particular esters thereof, and sequestering agents such as EDTA.

The composition may also contain fillers such as, for example, mineral particles such as clays, silicas, metal oxides such as titanium dioxide or zinc oxide, or mica, and/or organic fillers such as particles of polyamide (nylon) and in particular those sold under the name Orgasol by the company Atochem; latices; polyethylene powders; acrylic copolymer-based microspheres, such as those made of ethylene glycol dimethacrylate/lauryl methacrylate copolymer, sold by the company Dow Corning under the name Polytrap; poly(methyl methacrylate) microspheres, sold under the name Microsphere M-100 by the company Matsumoto or under the name Covabead LH85 by the company Wackherr; ethylene/acrylate copolymer powders, such as those sold under the name Flobeads by the company Sumitomo Seika Chemicals; expanded powders such as hollow microspheres, and in particular the microspheres formed from a vinylidene chloride/acrylonitrile/methacrylate terpolymer and sold under the name Expancel by the company Kemanord Plast; powders of natural organic materials, such as starch powders, in particular crosslinked or noncrosslinked maize, wheat or rice starch powders, such as the powders of starch crosslinked with octenylsuccinate anhydride, sold under the name Dry-Flo by the company National Starch; silicone resin microbeads such as those sold under the name Tospearl by the company Toshiba Silicone, in particular Tospearl 240; and mixtures thereof. The amount of filler(s) can range, for example, from 0.05% to 20% by weight, and better still 0.1% to 10% by weight, relative to the total weight of the composition.

As indicated above, this composition is intended to be used in a peeling process aimed at reducing the visible and/or tactile irregularities of the skin, and in particular at reducing wrinkles and fine lines and/or pigmentary marks and/or scars, in particular acne marks, and/or at unblocking the pores of the skin and giving the skin a more radiant look. The composition can therefore be applied in particular to the face and/or the neck and/or the neck and shoulders and/or the hands and/or the back.

In order to optimize its effects, the peeling process according to the invention preferably comprises additional steps of preparing the skin for the peeling and/or of caring for the skin after peeling, using compositions containing smaller amounts of surfactants than the peeling composition described above, or using compositions containing hydroxy acids.

The implementation of the above preliminary step also makes it possible to screen for any possible allergy to the surfactants and to improve the effectiveness and the homogeneity of the peel.

Thus, according to a specific embodiment, the process according to the invention can comprise, in addition to the steps mentioned above:

a preliminary step of applying, to the skin, a composition comprising, in a physiologically acceptable medium, from 1% to 15% by weight of one or more surfactants comprising at least one alkyl chain having from 6 to 16 carbon atoms, relative to the total weight of the composition, before the implementation of step (a), and/or just once or repeated up to five times if necessary, the peel sessions preferably being separated by one to eight weeks.

The composition of the invention can also be used in a pre-treatment or post-treatment step of a peel with a composition containing active peeling agents normally used, such as hydroxy acids or urea and its derivatives, or alternately with these peels.

A subject of the invention is also the use of the composition as defined above, in a pre-treatment or post-treatment step of a peel with a composition containing at least one peeling agent which is not a surfactant.

The composition according to the invention can be part of a kit comprising another peeling composition which will be used before or after the composition according to the invention.

More particularly, the other peeling composition can be a conventional peeling composition containing the active agents normally used for a peel, which are not surfactants.

Thus, a subject of the invention is also a kit comprising:
a first packaging comprising a peeling composition according to the invention,
a second packaging comprising a peeling composition comprising at least one peeling agent which is not a surfactant. This peeling agent can be chosen in particular from conventional peeling agents such as α-hydroxy acids and β-hydroxy acids.

The invention will now be illustrated by means of the following nonlimiting examples. The amounts are indicated as active material (AM) and not as starting materials.

In these examples, the amounts are indicated as percentage by weight.

|  | Example 1 | Example 2 | Example 3 | Example 4 | Example 5 |
|---|---|---|---|---|---|
| PEG-6 caprylic/capric glyceride (1) | 13 | — | — | — | — |
| Cocoglucoside (2) | — | 13 | — | — | — |
| Cocobetaine (3) | — | — | 20 | — | — |
| Lauryl ether sulphate (4) | — | — | — | 50 | — |
| Sodium cocoyl glycinate (5) | — | — | — | — | 15 |
| Cocoamphodiacetate (6) | — | — | — | — | 20 |
| Glycerol | — | 10 | — | — | — |
| Carbomer | — | — | 1 | — | — |
| EDTA | — | — | — | — | 1 |
| Base or acid | qs pH 6.6 | qs pH 7 | qs pH 7 | qs pH 4 | qs pH 7.5 |
| Water | qs 100 | qs 100 | qs 100 | qs 100 | qs 100 |

(1) Softigen 767 from the company Sasol (at 100% with respect to active material)
(2) 24.53% of Plantacare 818 UP from the company Cognis, which is at 53% with respect to active material
(3) 66.67% of Dehyton AB 30 from the company Cognis, which is at 30% with respect to active material
(4) 71.43% of Texapon AOS 225 UP from the company Cognis, which is at 70% with respect to active material
(5) 50% of Amilite GCS 12 from the company Ajinomoto, which is at 30% with respect to active material
(6) 64.52% of Miranol C 2 M Conc. NP from the company Rhodia, which is at 31% with respect to active material an additional step of applying, to the skin, a composition containing, in a physiologically acceptable medium, from 15% to 70% by weight of surfactants comprising at least one alkyl chain having from 6 to 16 carbon atoms, relative to the total weight of the composition, after the implementation of step (c).

The compositions used in these preliminary and additional steps can be applied in the morning and in the evening, for example, optionally in combination with a composition intended to protect the skin against the effects of UV radiation. The pre-treatment composition can be applied for one to four weeks, and the post-treatment composition for one day to eight weeks, for example.

The process according to the invention, including the optional preliminary and additional steps, can be carried out Protocol: The surfactants of the invention were solubilized in water or, when the surfactants were in aqueous solution, these solutions were simply diluted. The other cosmetic ingredients were added to the surfactant solutions. The pH of the solutions was adjusted, with sodium hydroxide or hydrochloric acid, to the pH indicated.

The compositions obtained were used according to the process described above.

Desquamating Effect of the Surfactants of the Invention

The desquamating effect of the surfactants was demonstrated in the following way:

An acetone powder of stratum corneum obtained by the varnish stripping technique, as described by B. Mehul et al. (2000, the Journal of Biological Chemistry, Vol. 275, No. 17, 12841-12847), was incubated with a solution of surfactant at a rate of 100 µl of solution per mg of acetone powder. The incubations were carried out in a 0.1 M Tris-HCl buffer, pH 8, at 30° C., for 8 hours with stirring. A control T0 was carried out, and also a control which was buffer alone.

The soluble proteins of each sample were then extracted under denaturing conditions (SDS, DTT and boiling), and the stable proteins were assayed according to the Bradford method; the concentrations were brought to 0.6 mg/ml in the same Laemmli extraction buffer.

An SDS-Page separation was then carried out, followed by blotting onto a PVDF membrane sold by Millipore. The corneodesmosin was immunodetected with the G3619 monoclonal antibody described in G. Serre et al. (1991, J. Invest. Dermatol., 97, 1061-1072) diluted to 1/12 500th. A peroxidase-coupled anti-mouse secondary antibody was used, and also the ECL chemiluminescent reagent sold by Amersham Biosciences for visualizing blots.

The results are expressed as percentages of residual corneodesmosins and are given in the table below. After 8 hours (T8 hours), a decrease was observed, compared with time zero (T0), in the amount of corneodesmosins obtained with the surfactants, relative to the amount obtained with the control which does not contain surfactant, the latter being replaced with the buffer. This decrease demonstrates the desquamating activity of the surfactants of the invention, via the proteolytic degradation of the corneodesmosins.

|  | T0 | T8 hours | Residual corneodesmosins (%) |
| --- | --- | --- | --- |
| 13% of PEG-6 caprylic/capric glyceride | 167.6 | 60.9 | 36 |
| 13% of cocoylbetaine | 234.1 | 73.1 | 31 |
| Control | 481 | 417.7 | 87 |

The above written description of the invention provides a manner and process of making and using it such that any person skilled in this art is enabled to make and use the same, this enablement being provided in particular for the subject matter of the appended claims, which make up a part of the original description and including a process for the treatment of visible and/or tactile irregularities of human skin, comprising:
  (a) applying topically, to the skin, a composition comprising, in a physiologically acceptable medium, at least 5% by weight of one or more surfactants comprising at least one alkyl chain having from 6 to 16 carbon atoms, relative to the total weight of the composition,
  (b) leaving the composition in contact with the skin for a period of time sufficient for the composition to act, and
  (c) optionally, removing the composition by rinsing.

Also fully enabled herein is a process as above but further comprising a preliminary step of applying to the skin a preliminary composition comprising, in a physiologically acceptable medium, from 1% to 15% by weight of one or more surfactants comprising at least one alkyl chain having from 6 to 16 carbon atoms, relative to the total weight of the composition, before topically applying to the skin a composition comprising a physiologically acceptable medium and at least 5% by weight relative to the total weight of the composition of one or more surfactants comprising at least one alkyl chain having from 6 to 16 carbon atoms, wherein the preliminary composition and the composition are different from one another, for example in the amount of one or more surfactants comprising at least one alkyl chain having from 6 to 16 carbon atoms therein.

As used herein, the phrases "selected from the group consisting of," "chosen from," and the like include mixtures of the specified materials. Terms such as "contain(s)" and the like as used herein are open terms meaning 'including at least' unless otherwise specifically noted. Phrases such as "mention may be made," etc. preface examples of materials that can be used and do not limit the invention to the specific materials, etc., listed.

All references, patents, applications, tests, standards, documents, publications, brochures, texts, articles, etc. mentioned herein are incorporated herein by reference. Where a numerical limit or range is stated, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein. In this regard, certain embodiments within the invention may not show every benefit of the invention, considered broadly.

The invention claimed is:

1. A cosmetic process for the treatment of human skin, comprising:
  topically applying to the skin a composition by at least one selected from the group consisting of fingers, cotton wool, a cotton wool bud, a brush, a gauze, a spatula and spraying, with the proviso that a pad is specifically excluded for the topical application,
  the composition comprising:
  a physiologically acceptable medium;
  from 15 to 70% by weight relative to the total weight of the composition of one or more surfactants selected from the group consisting of PEG-6 caprylic/capric glyceride, cocoglucoside, cocobetaine, lauryl ether sulphate, sodium cocoyl glycinate and cocoamphodiacetate; and
  0.01 to 5% by weight relative to the total weight of the composition of a hydrophilic polymer selected from the group consisting of a polycarboxyvinyl polymer, an acrylic copolymer, a polyacrylamide and an acrylamide copolymer;
  leaving the applied composition in contact with the skin for a period of time of at least 5 minutes, which is sufficient for the composition to act on and reduce visible irregularities of the skin, tactile irregularities of the skin or both visible and tactile irregularities;
  wherein
  the applied composition is free of a hydroxy acid,
  the pH of the applied composition is from 3.5 to 7,
  the composition does not include silica, and
  the composition is in the form of a gel, lotion or emulsion.

2. The process according to claim 1, wherein the applied composition comprises at least 20% by weight of water relative to the total weight of the composition.

3. The process according to claim 1, wherein the content of the one or more surfactants is 15% to 60% by weight relative to the total weight of the composition.

4. The process according to claim 1, wherein the applied composition further comprises from 1 to 50% by weight of at least one of ethanol and glycerol.

5. The process according to claim 1, wherein the pH of the applied composition is from 4.0 to 7.

6. The process according to claim 1, wherein the applied composition is left in contact with the skin for a period of between 5 minutes and 12 hours.

7. The process according to claim 1, further comprising applying to the skin a preliminary composition comprising:
a physiologically acceptable medium and
at least one surfactant comprising at least one alkyl chain having from 6 to 16 carbon atoms;
wherein
a content of the at least one surfactant comprising at least one alkyl chain having from 6 to 16 carbon atoms relative to the total weight of the preliminary composition, is 1 to 15% by weight, with the proviso that the content of the at least one surfactant comprising at least one alkyl chain having from 6 to 16 carbon atoms in the preliminary composition is less than the content of the one or more surfactants selected from the group consisting of PEG-6 caprylic/capric glyceride, cocoglucoside, cocobetaine, lauryl ether sulphate, sodium cocoyl glycinate and cocoamphodiacetate in the applied composition.

8. The process according to claim 1, further comprising:
removing the applied composition, and then applying to the skin an additional composition comprising:
a physiologically acceptable medium; and
at least one surfactant comprising at least one alkyl chain having from 6 to 16 carbon atoms.

9. The process according to claim 1, wherein the visible irregularities or tactile irregularities of the skin to be treated comprises at least one selected from the group consisting of wrinkles, fine lines, pigmentary marks, acne marks and blocked pores.

10. The process according to claim 1, wherein the skin to be treated is skin of a face, a neck, a neck and shoulders, hands and/or a back.

11. The process according to claim 1, wherein the applied composition is left in contact with the skin without further disturbance for at least 5 minutes.

12. The process according to claim 1, wherein the applied composition is one selected from the group consisting of an aqueous gel, an aqueous-alcoholic gel, and an aqueous-glycolic gel.

13. The process according to claim 1, wherein the action of the composition on visible irregularities of the skin, tactile irregularities of the skin or both visible and tactile irregularities is desquamation.

14. The process according to claim 1, comprising: topically applying to the skin the composition by at least one selected from the group consisting of fingers, a brush, a spatula and spraying.

* * * * *